United States Patent
Samaras et al.

(10) Patent No.: US 8,387,471 B2
(45) Date of Patent: Mar. 5, 2013

(54) DILUTER FOR EXHAUST GAS SAMPLING AND METHOD THEREFOR

(75) Inventors: Zissis Samaras, Thessaloniki (GR); Leonidas Ntziachristos, Thessaloniki (GR)

(73) Assignee: Aristotle University Thessaloniki Research Committee, Thessaloniki (GR)

( * ) Notice: Subject to any disclaimer, the term of this patent is extended or adjusted under 35 U.S.C. 154(b) by 633 days.

(21) Appl. No.: 12/449,591

(22) PCT Filed: Feb. 14, 2008

(86) PCT No.: PCT/GR2008/000010
§ 371 (c)(1),
(2), (4) Date: Aug. 14, 2009

(87) PCT Pub. No.: WO2008/099224
PCT Pub. Date: Aug. 21, 2008

(65) Prior Publication Data
US 2010/0058878 A1    Mar. 11, 2010

(30) Foreign Application Priority Data
Feb. 14, 2007  (GR) .................................. 070100103

(51) Int. Cl.
*G01N 1/00*    (2006.01)
(52) U.S. Cl. .......................................................... 73/863
(58) Field of Classification Search ............... 73/864.73, 73/864.74, 864.34, 23.31, 23.2; 436/180
See application file for complete search history.

(56) References Cited

U.S. PATENT DOCUMENTS

| 3,817,100 A | | 6/1974 | Anderson et al. ........... 73/861.63 |
| 4,586,367 A | | 5/1986 | Lewis ........................... 73/23.33 |
| 4,686,846 A | * | 8/1987 | Aramaki ....................... 73/23.32 |
| 5,184,501 A | | 2/1993 | Lewis et al. .................. 73/23.31 |
| 5,419,178 A | * | 5/1995 | Decker et al. ................ 73/23.31 |
| 5,469,731 A | * | 11/1995 | Decker et al. ................ 73/23.31 |
| 2004/0200265 A1 | * | 10/2004 | Eden et al. .................... 73/23.31 |

FOREIGN PATENT DOCUMENTS

EP    0532216    3/1993

* cited by examiner

*Primary Examiner* — Peter Macchiarolo
*Assistant Examiner* — Tamiko Bellamy
(74) *Attorney, Agent, or Firm* — James Creighton Wray

(57) ABSTRACT

A diluter apparatus and a method for sampling of exhaust gas of engines, wherein the diluter has a primary capillary connected to a primary stabilizing chamber. The primary stabilization chamber is kept at a pressure below ambient by means of a vacuum pump connected to the primary stabilization chamber by means of a primary outlet duct and where dilution air in the primary stabilization chamber is introduced by means of a primary dilution air duct through a primary mixing tip, wherein there is provided an excess flowrate arrangement for providing an exhaust gas flowrate in excess of the sample flowrate in the capillary. Exhaust gas flowrate totally surrounds the capillary inlet tip, wherein the primary capillary is immersed in the exhaust gas flowrate with flowrate arrangement, and wherein the diluter receives the exhaust gas via said primary capillary.

19 Claims, 2 Drawing Sheets

DILUTER FOR EXHAUST GAS SAMPLING AND METHOD THEREFOR

This application claims the benefit of Greek Application No. 20070100103 filed Feb. 14, 2007 and PCT/GR2008/000010 filed Feb. 14, 2008, which are hereby incorporated by reference in their entirety.

FIELD OF THE INVENTION

The present invention relates to a device used for the dilution of exhaust gas as a so-called diluter, and in particular for engines. More particularly, the invention relates to a device and a method which is able to maintain a constant dilution ratio regardless of the exhaust gas backpressure in the exhaust line.

BACKGROUND OF THE INVENTION

Diluters are necessary in the process of exhaust sampling, before the exhaust is led to instrumentation for analysis. In particular, diluters reduce the temperature and the humidity of the exhaust gas which, otherwise, might not be tolerated by the analytical instrumentation. In addition they reduce the concentration of pollutants and equilibrate the sample before analysis.

Exhaust gas dilution may be achieved with the use of full flow diluters, wherein all of the exhaust gas is led to a dilution tunnel where it mixes with ambient filtered air before analysis. Such dilution systems include the constant volume sampling technique, as described in legislation 91/441/EEC of the European Commission (Official Journal L 242, Aug. 30, 1991 P. 0001-0106). Constant volume, full flow diluters lead to variable dilution ratios over transient tests, as the mixing proportions of exhaust gas and dilution air change, depending on the momentary flowrate of exhaust gas. The variable dilution ratio is a significant shortcoming when it comes to the accurate characterization of emissions, in particular of particulate matter emissions, because it introduces variable degrees of particle nucleation and condensation, depending on the saturation ratio of volatile and semi-volatile species following dilution.

To overcome the issue of variable dilution ratio, partial flow sampling systems have become widespread, where only a portion of the exhaust gas is sampled, measured and conditioned with a measured quantity of dilution air, to provide a fixed dilution ratio. The dilution ratios typically achieved by such systems range from 10:1 to 1000:1. This wide range is required to reduce particle levels from different sources, such as conventional diesel engines, diesel with particle filters within the measuring range of the available instrumentation. Such partial flow systems are described for example in the patent applications US2003/0232449A1, JP2004205253A2004.T.22. These devices mainly target at sampling exhaust downstream of aftertreatment devices because the dilution ratio provided is very sensitive to the exhaust gas pressure variation. Upstream of aftertreatment devices and, in particular, of diesel particle filters, the exhaust backpressure may vary between a few millibars to several hundreds of millibars above ambient, resulting in significant variation of the dilution ratio.

The device presented in patent CH693491 addresses the issue of providing a constant dilution ratio with small sensitivity to upstream exhaust gas conditions but introduces a number of moving parts, which are not desirable for the dilution of the hot, humid and particle laden exhaust gas.

AIM OF THE INVENTION

The purpose of the present invention is to dilute the exhaust gas, providing a constant dilution ratio, regardless of the upstream exhaust gas pressure, without using any moving parts. The proposed diluter utilizes a very small fraction of the exhaust gas (of the order of 0.5 lpm), which is sampled through a capillary duct. Due to the very low exhaust quantity, no tight fixation between the diluter and the exhaust line is required but the capillary may be only immersed to the exhaust flow, which is otherwise freely exhausting to the atmosphere. In this respect, the capillary inlet is always exposed to an almost ambient pressure, regardless of the pressure of the exhaust gas, which leads to a constant dilution ratio. The sample flowrate through the capillary is achieved by maintaining a regulated underpressure at the capillary outlet. The diluted exhaust is then collected in a stabilization chamber, where temperature, humidity and residence time may be adjusted to condition the collected aerosol at will. A different dilution ratio setting may be achieved by appropriately adjusting the underpressure in the stabilization chamber. Multiple capillaries and stabilization chambers may be cascaded to increase the dilution ratios. After the final dilution stage, particle samples may be collected on a filter for gravimetric determination or analyzed by number counters, surface monitors or any other technique utilized for the physical or chemical characterization of particles.

SUMMARY OF THE INVENTION

In a preferred embodiment the capillary duct is realized with a hypodermic needle and two cascaded hypodermic needles/stabilization chambers are combined to provide the desired dilution ratio. The diluter location is fixed relative to the vehicle/engine exhaust line and the needle is inserted in the exhaust line. This embodiment may be used to dilute aerosol from any engine or vehicle configuration, such as compression-ignition engines, spark-ignition engines, and complete vehicle exhaust lines.

In another embodiment, exhaust gas may be led to the diluter's capillary duct by means of two probes, located respectively upstream and downstream of any aftertreatment device, which needs to be characterized. The probes are of appropriate diameter to provide a total exhaust gas flowrate marginally higher than the flowrate in the first hypodermic needle. The excess flowrate is exhausted to the atmosphere under constant pressure. By means of shut-off valves, exhaust gas may be fed to the diluter's capillary by either the upstream or the downstream probe, thus providing an estimate of the filtration efficiency of the device.

DESCRIPTION

Figure 1:
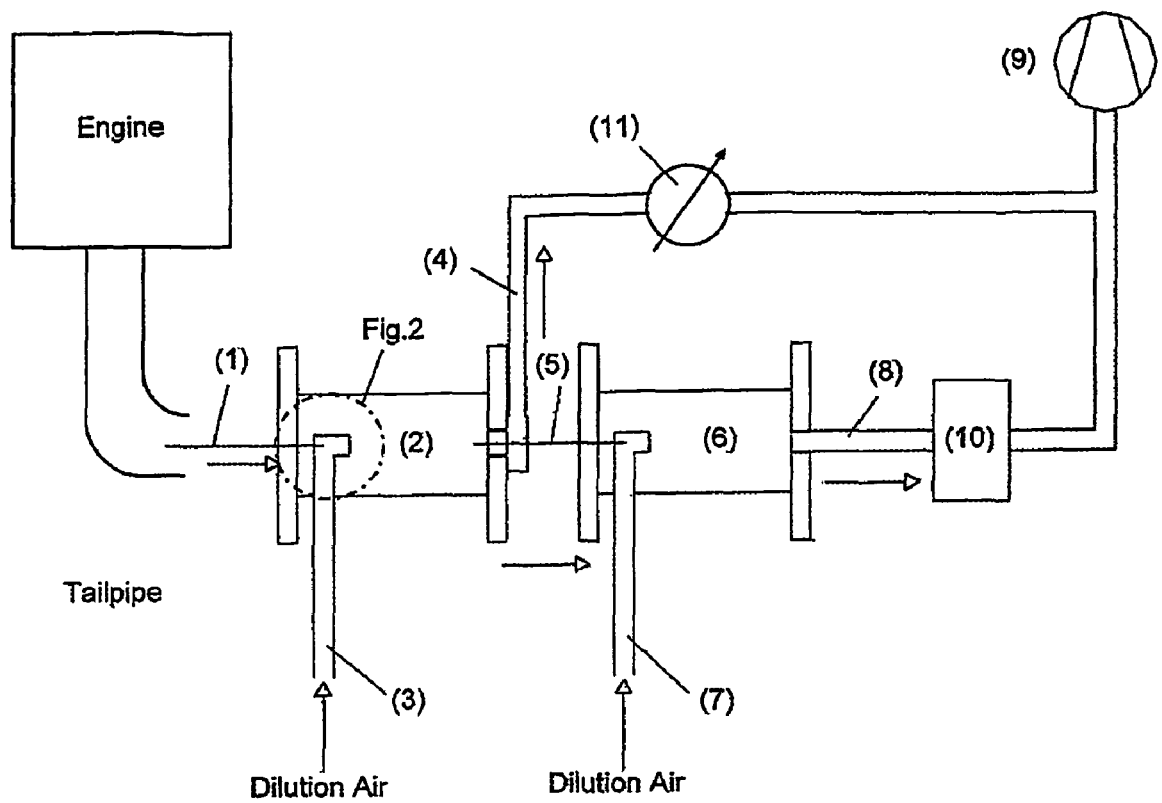
FIG. 1 illustrates a first embodiment of the invention. It shows the primary (1) and the secondary capillary (5) and the primary (2) and the secondary (6) stabilization chamber. The exhaust is drawn by means of the pump (9) from the tailpipe to the measurement instrumentation after conditioning in the stabilization chambers (2), (6).

With reference to FIG. 1, number (1) designates the primary capillary, which draws the undiluted exhaust in the primary stabilization chamber (2). The dilution in the primary stabilization chamber is conducted by introducing dilution air through the primary dilution air duct (3). The sample through the primary capillary (1) and the dilution air through the primary dilution air duct (3) are introduced in the primary stabilization chamber (2) due to the underpressure in the chamber. The underpressure in the primary stabilization chamber (2) is produced by the pump (9) drawing air through the primary outlet duct (4). The dilution ratio (typically in the order of 20:1) and the residence time (typically in the order of 0.5-1.0 s) of the sample in the primary stabilization chamber (2) may be adjusted by means of the throttling mechanism (11), which may be any appropriate regulation valve or mass flow controller. The stabilization of the sample in the primary stabilization chamber is necessary to allow for homogenous mixing of the exhaust components with the dilution air and for temperature equilibration.

Since the primary capillary (1) tip is at ambient pressure, the flowrate through the primary capillary (typically in the order of 0.5 lpm) depends only on the pressure in the primary stabilization chamber (2), the dilution air flowrate through the primary dilution air duct (3), typically in the order of 10 lpm, and, to a lower degree, the temperature of the exhaust gas in the tailpipe. The underpressure and the primary dilution air flowrate are implicitly associated by the characteristic curve of the pump (9) and throttling mechanism (11) utilized. Therefore, at steady-state engine operation with constant exhaust gas temperature, the dilution ratio in the primary stabilization chamber (2) only depends on the setting of the throttle mechanism (11).

In order to further increase the dilution ratio, if so desired for high particle concentrations in the tailpipe, a secondary capillary (5) is firmly connected to the primary stabilization chamber (2), leading the primary diluted sample to a secondary stabilization chamber (6). The flowrate from the primary (2) to the secondary stabilization chamber (6) is achieved by developing a higher underpressure in the secondary stabilization chamber (6), compared to the primary stabilization chamber (2). This may be achieved by connecting the pump (9) to the secondary stabilization chamber (6) through the sample duct (8), without any intervening resistance, but using only the instrument/technique employed for particle characterization (10). The total dilution ratio in this configuration depends, in addition to the variables mentioned in the previous paragraph, on the pressure difference between the secondary (6) and the primary (2) stabilization chambers and the total flowrate required by the particle measurement unit (10), through the sample duct (8). This first embodiment may be applied when the variation of exhaust pressure and temperature in the tailpipe is limited and when the dilution ratio needs not be precisely regulated.

Figure 2:
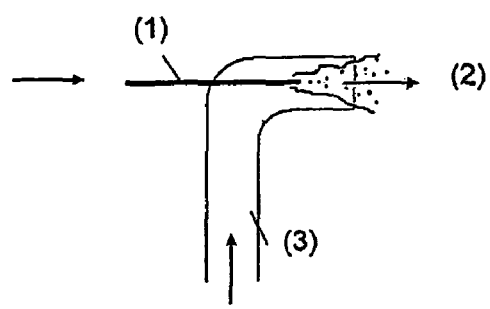
FIG. 2 shows a detail of the primary mixing tip formed by the primary capillary (1) exhausting the sample in the primary dilution air duct (3), upstream of the duct's outlet tip.

In order to minimize particle losses, to stabilize the flowrate in the capillary and to improve the mixing of the sample with the dilution air, a mixing tip is formed upstream of the stabilization chamber. This is shown in some detail in FIG. 2. In the mixing tip, the sample flowrate from the primary capillary (1) is first exposed to the flowrate of the dilution air that flows in the primary dilution air duct (3). The primary dilution air duct (3) forms a 90° bend before the dilution air expands in the stabilization chamber. The capillary outlet tip is located along the axis of the primary dilution air duct (3), downstream of the bend and upstream of the primary dilution air duct tip. A similar mixing tip is also formed downstream of the secondary capillary (5).

Figure 3:
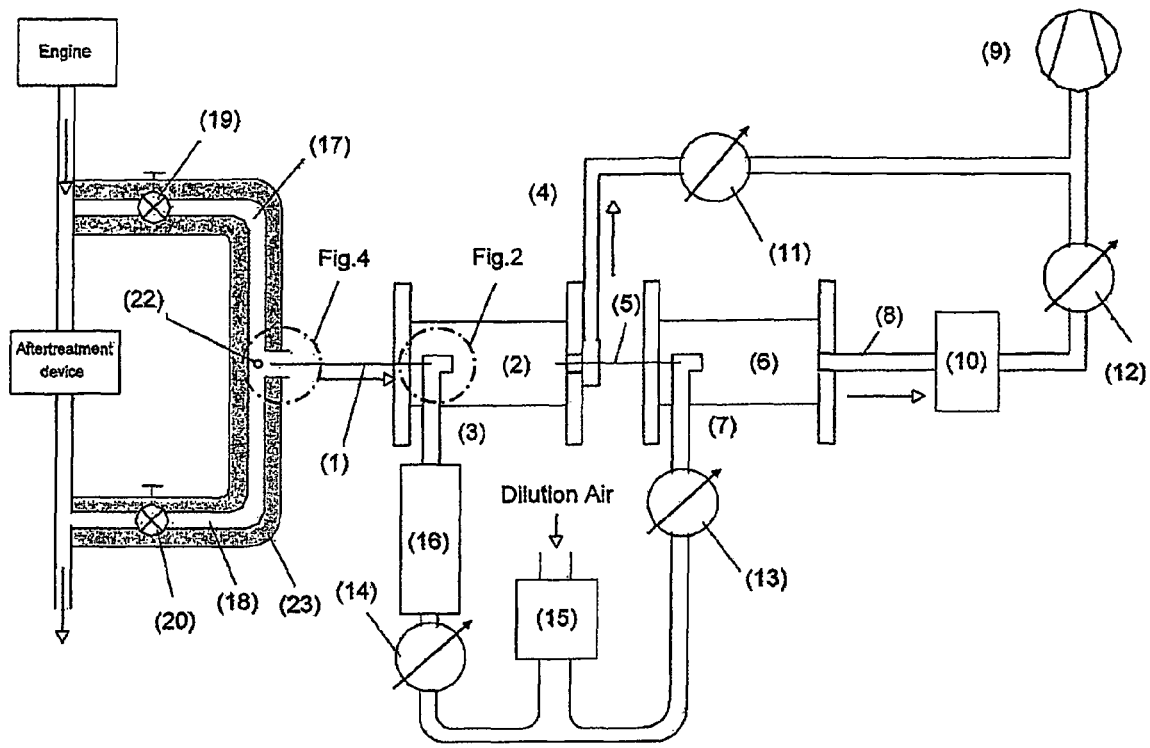
FIG. 3 illustrates a second embodiment of the invention. In this embodiment, the flow resistance of the primary (3) and secondary (7) dilution air ducts, as well as the sample outlet (8) are independently adjusted by means of the throttling mechanisms (14), (13) and (12). An excess flowrate arrangement, detailed in FIG. 4, is also used to consecutively sample exhaust upstream and downstream of an aftertreatment device.

FIG. 3 demonstrates a second embodiment which is preferred in measurements where, for example, a larger variation of the exhaust gas pressure and temperature is expected and where a higher precision is required for the dilution ratio adjustment. In this embodiment, the primary capillary (1) is exposed to a small exhaust gas flowrate drawn from the exhaust line via the transfer lines (17) or (18). The primary capillary is not fixed to the exhaust pipe, which is allowed to freely exhaust in the atmosphere under ambient pressure.

Figure 4:
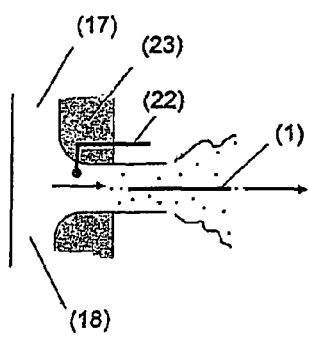
FIG. 4 shows the excess flow arrangement with the primary capillary (1) inlet tip immersed and surrounded by the exhaust flowrate, while the exhaust flowrate freely exhausts to the atmosphere.

FIG. 4 shows a detail of excess flow arrangement where the primary capillary (1) samples from the outlet of the transfer lines (17) and (18). The primary capillary (1) is fully immersed and surrounded by the exhaust gas flow just before (e.g. 10 mm) this is expanded in the atmosphere. The sample flowrate in the transfer line outlet is in excess of the sample flowrate in the primary capillary (1) and its pressure at the sampling level is quasi ambient. The temperature of the exhaust gas at the sampling tip can be adjusted by means of the heating element (23) and is measured by the temperature sensing element (22). Samples may be drawn from different locations along the exhaust line, e.g. downstream and upstream of an aftertreatment device via activation of the shut-off valves (19) and (20).

Dilution in the primary (2) and secondary (6) stabilization chambers takes place as described in the first embodiment. In order to achieve a more precise regulation of the dilution ratio, the dilution air flowrate through the primary (3) and secondary (7) dilution air ducts is regulated by means of the throttling mechanisms (14) and (13) respectively. In addition, the flowrate pumped out of the system is regulated by means of the throttle vanes (11) and (12). The dilution ratio calculation in this case has to take into account the setting of these valves as well. In comparison to previous art, this embodiment has the advantage of being able, without any moving parts, to maintain a constant dilution ratio which depends on the setting of the throttle valves (11), (12), (13), (14) and the pump (9) only and is independent of the temperature and the pressure of the exhaust gas in the tailpipe.

Furthermore, if additional conditioning of the sample is required, a temperature adjusting element (16) may intervene in the primary dilution air duct (3) downstream of the throttling mechanism (14), to regulate the temperature of the primary dilution air. Also, a dilution air purifying unit (15) may be used to control the impurities and the humidity of the dilution air.

The invention claimed is:

1. A diluter for sampling of exhaust gas, of engines, comprising a primary capillary (1) connected to a primary stabilization chamber (2), which said primary stabilization chamber is kept at a pressure below ambient by means of a vacuum pump (9) connected to said primary stabilization chamber by means of a primary outlet duct (4) and where dilution air in said primary stabilization chamber is introduced by means of a primary dilution air duct (3) through a primary mixing tip, wherein there is provided an excess flowrate arrangement for providing an exhaust gas flowrate in excess of the sample flowrate in said capillary (1), which exhaust gas flowrate totally surrounds said capillary inlet tip, wherein said primary capillary (1) is immersed in the exhaust gas flowrate with said flowrate arrangement, wherein said diluter receives the exhaust gas via said primary capillary (1).

2. The diluter according to claim 1, wherein there is provided a throttling mechanism (11) by means whereof a dilution ratio and the residence time of the sample of the primary stabilization chamber (2) is adjusted.

3. The diluter according to claim 1 wherein there is provided a secondary stabilization chamber (6) and a secondary capillary (5) which is immersed in the primary stabilization chamber (2) for leading the sample from said primary stabilization chamber (2) to said secondary stabilization chamber (6) which is kept at a pressure below the pressure of the primary stabilization chamber (2) and wherein there is provided a sample duct (8) for achieving this low pressure by drawing the sample from said sample duct (8) using the said pump (9) or a different vacuum pump and wherein there is provided a secondary dilution air duct (7) and a secondary mixing tip for introducing dilution air in said secondary stabilization chamber (6) through said secondary mixing tip.

4. The diluter according to claim 1, wherein each said mixing tip is formed by an alignment of an axis of the corresponding capillary (5) with the axis of the corresponding dilution air duct (7) respectively, wherein the sample flow carried by said capillary is exposed to the dilution air flow upstream of outlet tip of the said dilution air duct.

5. The diluter according to claim 3, wherein there are provided throttling mechanisms (14, 13), which enable an adjustment of the resistance to flow of the primary dilution air duct (3) and the secondary dilution air duct (7) respectively to be independent, and/or throttling mechanisms (11, 12) enabling an adjustment of the resistance to flow of the primary outlet duct (4) and the sample outlet duct (8), respectively to be independent.

6. The diluter according to claim 1, wherein there is provided a heating element (23) and a temperature sensing element (22), so as to enable the temperature of the exhaust gas at the sampling tip to be adjusted by means of the heating element (23) and to be measured by the temperature sensing element (22).

7. The diluter according to claim 1, wherein multiple capillaries and stabilization chambers are arranged in cascade to increase the dilution ratios.

8. The diluter according to claim 1, wherein the capillary duct is a hypodermic needle, wherein at least two cascaded hypodermic needles and two stabilization chambers are combined to provide the desired dilution ratio.

9. The diluter according to claim 8, wherein the diluter location is fixed relative to the engine exhaust line and the needle is inserted in the exhaust line.

10. Method for sampling of exhaust gas of engines, notably for working out a diluting device as defined in one of the preceding claims, wherein said stabilization chamber is kept at a pressure below ambient by means of a vacuum pump (9), and where dilution air in said stabilization chamber is introduced by means of said primary dilution air duct (3) through a primary mixing tip, in that said diluter receives the exhaust gas via the primary capillary (1) which is immersed in the exhaust gas flowrate with said excess flowrate arrangement, which provides an exhaust gas flowrate in excess of the sample flowrate in the said capillary, which exhaust gas flowrate totally surrounds said capillary inlet tip.

11. Method according to claim 10 wherein said secondary capillary (5) is immersed in the primary stabilization chamber (2) and leads the sample from said stabilization chamber (2) to a secondary stabilization chamber (6) which is kept at a pressure below the pressure of the primary stabilization chamber (2) and where this low pressure is achieved by drawing the sample from a sample duct (8) using the said pump (9) and where dilution air is introduced in said secondary stabilization chamber (6) by means of a secondary dilution air duct (7) through a secondary mixing tip.

12. Method according to claim 11, wherein a finite residence time required for mixing and temperature equilibration is generated by the primary (3) and secondary (6) stabilization chambers.

13. Method according to claim 10, wherein the temperature of the dilution air in the primary dilution air duct (7) is adjusted independently, selectively, from the temperature of the dilution air in the secondary dilution air duct (7).

14. Method according to claim 10, wherein a substantially constant dilution ratio is generated, regardless of the upstream exhaust gas pressure, without using any moving parts.

15. Method according to claim 10, wherein a very small fraction of the exhaust gas, of the order of 0.5 lpm, is utilized by said diluter, which is sampled through said capillary duct.

16. Method according to claim 10, wherein a regulated underpressure is maintained at the capillary outlet (7) and in that the diluted exhaust is then collected in said stabilization chamber.

17. Method according to claim 10, wherein after the final dilution stage, particle samples are collected on a filter for gravimetric determination or analyzed by number counters or surface monitors.

18. Method according to claim 10, wherein exhaust gas is led to the diluter's capillary duct by means of two probes, located respectively upstream and downstream of an after treatment device to be characterized, wherein said probes are of appropriate diameter to provide a total exhaust gas flowrate marginally higher than the flowrate in the first hypodermic needle, the excess flowrate is exhausted to the atmosphere under constant pressure, and exhaust gas is fed to the diluter's capillary by either the upstream or the downstream probe by means of shut-off valves, so as to provide an estimate of the filtration efficiency of the device.

19. Use of the device according to claim 9, to dilute aerosol from any engine or vehicle configuration, compression-ignition engines, spark-ignition engines, and complete vehicle exhaust lines.

* * * * *